US011865228B2

(12) United States Patent
Ho et al.

(10) Patent No.: US 11,865,228 B2
(45) Date of Patent: Jan. 9, 2024

(54) BONE VOID FILLER AND METHOD FOR MANUFACTURING THE SAME BY NATURAL CALCIUM-CONTAINING WASTE

(71) Applicant: NATIONAL UNIVERSITY OF KAOHSIUNG, Kaohsiung (TW)

(72) Inventors: Wen-Fu Ho, Kaohsiung (TW); Hui-Chun Yu, Kaohsiung (TW); Shih-Ching Wu, Kaohsiung (TW); Hsueh-Chuan Hsu, Kaohsiung (TW); Chi-Jen Chung, Kaohsiung (TW); Shih-Kuang Hsu, Kaohsiung (TW)

(73) Assignee: National University Of Kaohsiung, Kaohsiung (TW)

( * ) Notice: Subject to any disclaimer, the term of this patent is extended or adjusted under 35 U.S.C. 154(b) by 364 days.

(21) Appl. No.: 17/366,721

(22) Filed: Jul. 2, 2021

(65) Prior Publication Data

US 2023/0001050 A1   Jan. 5, 2023

(51) Int. Cl.
*A61L 27/36* (2006.01)
*A61L 27/20* (2006.01)
*A61L 27/12* (2006.01)
*A61L 27/56* (2006.01)

(52) U.S. Cl.
CPC .............. *A61L 27/365* (2013.01); *A61L 27/12* (2013.01); *A61L 27/20* (2013.01); *A61L 27/3637* (2013.01); *A61L 27/3687* (2013.01); *A61L 27/3691* (2013.01); *A61L 27/56* (2013.01)

(58) Field of Classification Search
CPC ........ A61L 27/356; A61L 27/20; A61L 27/12; A61L 27/56
See application file for complete search history.

(56) References Cited

U.S. PATENT DOCUMENTS

2017/0252480 A1*  9/2017  Ishikawa ................. A61L 27/02

FOREIGN PATENT DOCUMENTS

| CN | 1836741 A    | 9/2006 |
| CN | 108395236 A  | 8/2018 |
| TW | I494270 B    | 8/2015 |
| TW | I598118 B    | 9/2017 |
| TW | I656248 B    | 4/2019 |

* cited by examiner

*Primary Examiner* — Jason-Dennis N Stewart
(74) *Attorney, Agent, or Firm* — Rosenberg, Klein & Lee (57) ABSTRACT

The present invention discloses a bone void filler and a method for manufacturing the same by natural calcium-containing waste, which comprises steps of mixing 5-20 wt % of a calcium-containing waste powder, 5-20 wt % of acetic acid and a remaining weight percentage of water uniformly to obtain a mixing solution; adding 5-20 vol % of a diammonium hydrogen phosphate solution to the mixing solution to obtain a suspension; controlling a pH value of the suspension to obtain an alkaline solution; leaving the alkaline solution at room temperature for precipitation for 0.1 to 72 hours, centrifuging or suction filtrating the alkaline solution to obtain a precipitate, drying and grinding the precipitate to obtain hydroxyapatite; and mixing 30-60 wt % of a pore former and 30-60 wt % of the hydroxyapatite and a remaining weight percentage of a binder uniformly to form a mixture, compression molding the mixture in a mold and sintering the compression-molded mixture.

10 Claims, 9 Drawing Sheets

BONE VOID FILLER AND METHOD FOR MANUFACTURING THE SAME BY NATURAL CALCIUM-CONTAINING WASTE

BACKGROUND OF THE INVENTION

1. Field of the Invention

The present invention relates to a bone void filler and a method for manufacturing the same by natural calcium-containing waste, wherein the natural calcium-containing waste is used to manufacture bone void fillers such as porous particles or porous scaffolds so as to achieve effects of recycling waste and reducing production cost.

2. Description of Related Art

Calcium phosphate ceramic has great bioactivity, biocompatibility and bioabsorbability, and is usually used as biomedical materials, such as dental fillings, orthopedic fillers, drug carriers and scaffolds for tissue engineering.

Commonly used calcium phosphate ceramic comprises hydroxyapatite (HA), β-tricalcium phosphate (β-TCP) and α-tricalcium phosphate (α-TCP). In the Taiwan Pat. No. 1494270(B) issued on 1 Aug. 2015, a method for synthesis hydroxyapatite is disclosed. The hydroxyapatite is manufactured with calcium-containing biological wastes and trace plant extract, and has great biocompatibility. The calcium-containing biological wastes comprise eggshell and shell of oyster. In addition, the Taiwan Pat. No. I598118(B) issued on 11 Sep. 2017 also disclosed a chitin-hydroxyapatite composite material and its manufacturing method. The manufacturing method comprises the steps of incubating a micronized substrate in an acidic solution at room temperature in which the micronized substrate is selected from a group consisting of shells of the crustacean, carapaces of the crustacean, hard sheath of the mollusk and a combination thereof.

Hydroxyapatite is a main inorganic component of human bones and teeth. After thermal treatment, different phases of the hydroxyapatite are generated including β-TCP, α-TCP and tetracalcium phosphate (TTCP). A traditional manufacturing method of hydroxyapatite comprises steps of mixing a calcium-containing compound with a phosphorus containing compound to obtain a mixture and incubating the mixture in an alkaline condition, wherein the calcium-containing compound comprises calcium carbonate, calcium nitrate and calcium oxide. A commonly used synthesis method of hydroxyapatite comprises a hydrothermal method, a sol-gel method and a precipitation method. Although the hydrothermal method is the most commonly used to syntheses hydroxyapatite, it needs to use high-pressure equipment and a yield thereof is limited.

According to previous researches, a porous calcium phosphate ceramic material improves cell adhesion, vascularization and fluid circulation so as to improve bone formation. There are many methods to manufacture the porous calcium phosphate ceramic material, including a method using a pore former, a sponge replication method and a lyophilization method.

In view of a high demand of the porous calcium phosphate ceramic material in the dental fillings, the bone void fillers and the tissue engineering field, a porous calcium phosphate having a better biodegradability, a high supportive ability and a low production cost for bone void fillers is still developed by the related industries.

SUMMARY OF THE INVENTION

The present invention relates to a bone void filler and a method for manufacturing the same by natural calcium-containing waste, wherein the natural calcium-containing waste is utilized to manufacture bone void fillers such as porous particles or porous scaffolds so as to achieve effects of recycling waste and reducing production cost.

The process for manufacturing a bone void filler with a natural calcium-containing waste comprises the steps of (a) mixing 5-20 wt % of a powder of calcium-containing waste, 5-20 wt % of acetic acid and a remaining weight percentage of water uniformly to obtain a mixing solution, wherein the powder of calcium-containing waste comprises an eggshell powder, a shell powder of *Crustacea* animals, a shell powder of *Bivalvia* animals or a shell of *Gastropoda* animals; (b) adding 5-20 vol % of a diammonium hydrogen phosphate solution into the mixing solution to obtain a suspension; (c) controlling a pH value of the suspension between 7.5 and 14 for obtainment of a strongly or weakly alkaline solution; (d) leaving the alkaline solution at room temperature for precipitation for 0.1-72 hours, preforming a centrifugal process or a suction filtration process on the alkaline solution to obtain a precipitate, drying and grinding the precipitate to obtain a hydroxyapatite; and (e) mixing 30-60 wt % of a pore former, 30-60 wt % of the hydroxyapatite and a remaining weight percentage of a binder uniformly to form a mixture, compression molding the mixture in a mold and then sintering the compression-molded mixture at a sintering temperature to obtain the bone void filler. The pore former is selected from a group consisting of polyvinylpyrrolidone (PVP), poly (lactic-co-glycolic acid) (PLGA), stearic acid, sucrose and graphite, and the binder is selected from a group consisting of starch, paraffin, carboxymethyl cellulose and poly (vinyl alcohol) (PVA).

The present invention also discloses a bone void filler manufactured by the abovementioned method.

In one embodiment of the present invention, the sintering temperature in the step (e) is raised to 200-500° C. at a heating rate of 1-5° C./min and is maintained for 1-5 hours; and then the sintering temperature is raised to 1000-1300° C. at the heating rate of 1-5° C./min and is maintained for 5-30 hours to obtain a biphasic material.

In a second embodiment of the present invention, the sintering temperature is increased to 200-500° C. at a heating rate of 1-5° C. per minute and is maintained for 2-5 hours; and the sintering temperature is further increased to 1000-1300° C. at the heating rate of 1-5° C. per minute and is maintained for 5-30 hours to obtain a biphasic material.

In another embodiment of the present invention, the sintering temperature is increased to 200-500° C. at a heating rate of 1-5° C. per minute and is maintained for 2-5 hours; and then the sintering temperature is increased to 1000-1500° C. at the heating rate of 1-5° C. per minute and is maintained for 1-10 hours to obtain a triphasic material.

In another embodiment of the present invention, the sintering temperature is increased to 300-500° C. at a heating rate of 1-5° C. per minute and is maintained for 2-5 hours; and then the sintering temperature is increased to 1300-1500° C. at the heating rate of 1-5° C. per minute and is maintained for 1-10 hours to obtain a triphasic material.

In one embodiment of the present invention, the *Crustacea* animals comprise crabs, shrimps, lobsters, crayfishes and hills, wherein the *Bivalvia* animals comprise *Ostreoida* animals and *Venerida* animals, and wherein the *Gastropoda* animals comprise *Haliotidae* animals, wherein the *Ostreoida* animals include clams, the *Venerida* animal include *Meretrix lusoria*, and the *Haliotidae* animals include different kinds of abalones.

Accordingly, the precipitation method is used in the present invention for manufacture of bone void fillers with high yield and low energy consumption and simple equipment. Therefore, the present invention enables to decrease a whole production cost for synthesis hydroxyapatite and has a better economic benefit when manufacturing bone void fillers by using the hydroxyapatite.

BRIEF DESCRIPTION OF THE DRAWINGS

FIG. 1(*a*) and FIG. 1(*b*) show scanning electron microscope photographs of a hydroxyapatite powder in the present invention;

FIG. 5(*a*) to FIG. 5(*c*) show scanning electron microscope photographs of a biphasic porous HA/β-TCP material in the present invention;

DETAILED DESCRIPTION OF THE PREFERRED EMBODIMENT

To provide a thorough understanding of the present invention, an exemplary embodiment of the present invention will be described in detail with reference to the accompanying drawings.

The present invention discloses a method for manufacturing a bone void filler by a natural calcium-containing waste which comprises steps of: (a) uniformly mixing 5-20 wt % of a powder of calcium-containing waste, 5-20 wt % of acetic acid and a remaining weight percentage of water to obtain a mixing solution; (b) adding 5-20 vol % of a diammonium hydrogen phosphate solution into the mixing solution to obtain a suspension; (c) controlling a pH value of the suspension between 7.5 and 14 to obtain an alkaline solution and the alkaline solution can be a strongly or weakly alkaline solution; (d) leaving the alkaline solution at room temperature for precipitation for 0.1-72 hours, preforming a centrifugal process or a suction filtration process on the alkaline solution to obtain a precipitate, drying and grinding the precipitate to obtain a hydroxyapatite; and (e) uniformly mixing 30-60 wt % of a pore former, 30-60 wt % of the hydroxyapatite and a remaining weight percentage of a binder to form a mixture, compression molding the mixture in a mold and then sintering the compression-molded mixture at a sintering temperature to obtain the bone void filler. The pore former is selected from a group consisting of polyvinylpyrrolidone (PVP), poly (lactic-co-glycolic acid) (PLGA), stearic acid, sucrose and graphite, and the binder is selected from a group consisting of starch, paraffin, carboxymethyl cellulose and poly (vinyl alcohol) (PVA).

Preferably, in the step (e), the sintering temperature is raised to 200-500° C. at a heating rate of 1-5° C./min and is maintained for 2-5 hours; and then the sintering temperature is raised to 1000-1300° C. at the heating rate of 1-5° C./min and is maintained for 5-30 hours to obtain a biphasic material.

In a second embodiment, the sintering temperature in the step (e) is raised to 200-500° C. at a heating rate of 1-5° C./min and is maintained for 2-5 hours; and then the sintering temperature is raised to 1000-1500° C. at the heating rate of 1-5° C./min and is maintained for 1-10 hours to obtain a triphasic material.

In addition, the powder of calcium-containing waste comprises an eggshell powder, a shell powder of *Crustacea* animals, a shell powder of *Bivalvia* animals or a shell powder of *Gastropoda* animals. The *Crustacea* animals include crabs, shrimps, lobsters, crayfishes and hills; the *Bivalvia* animals include *Ostreoida* animals and *Venerida* animals; and the *Gastropoda* animals include *Haliotidae* animals. Furthermore, the *Ostreoida* animals include clams, the *Venerida* animals include *Meretrix lusoria*, and the *Haliotidae* animals include different kinds of abalones.

The present invention also discloses a bone void filler manufactured by the abovementioned method.

The following exemplary embodiment provides the practical application scope of the present invention, but is not intend to limits the protection scope of this invention.

There are many kinds of calcium-containing wastes including sea shells, oyster shells and egg shells and most of these calcium-containing wastes are not properly utilized. In addition, the hydroxyapatite (HA) obtained from these calcium-containing wastes usually comprises trace elements so the hydroxyapatite is benefit to human. Furthermore, the hydroxyapatite obtained from these calcium-containing wastes also comprises carbonates in which the composition thereof is closer to the natural bone composition of human.

Embodiment 1

Manufacturing a Nano-Grade Hydroxyapatite Powder

Egg shells are cleaned, dried and ground to obtain an egg shell powder. Then, 12 wt % of the egg shell powder, 16 wt % of acetic acid and a remaining weight percentage of water are mixed, and the egg shell powder is then dissolved to obtain a mixing solution. After that, 10 vol % of a diammonium hydrogen phosphate solution is added into the mixing solution to obtain a suspension. A pH value of the suspension is adjusted to pH 10 by uniformly mixing with an ammonia solution to obtain an uniformly-mixed alkaline solution, and the alkaline solution can be a strongly alkaline solution or a weakly alkaline solution. The uniformly-mixed alkaline solution is left at room temperature for precipitation for 6-18 hours. After precipitation, the uniformly-mixed alkaline solution is centrifuged to obtain a precipitate. Additionally, a suction filtration process can be performed on the uniformly-mixed alkaline solution to obtain the precipitate.

The precipitate is then dried and grinded to obtain a nano-grade hydroxyapatite powder.

The abovementioned method has a 80% yield of the nano-grade hydroxyapatite powder. Crystal grains of the nano-grade hydroxyapatite powder have grain sizes between 10 nm and 25 nm and a crystallinity between 10% and 30%. In addition, the crystal grains have a width between 10 nm and 45 nm and a length between 20 nm and 90 nm. The nano-grade hydroxyapatite powder comprises main elements including calcium, phosphorus, oxygen and carbon and trace elements including magnesium and strontium. In comparison with a hydroxyapatite synthesized using chemical agents (a calcium to phosphorus ratio of 1.67), the nano-grade hydroxyapatite powder of the present invention has a calcium to phosphorus ratio ranging from 1.4 to 1.6 which is closer to the calcium to phosphorus ratio of human bones. Moreover, the nano-grade hydroxyapatite of the present invention does not contain heavy metals which meets the requirement of ASTM F1581-08 of the American Society for Testing and Materials.

Figure 1A:
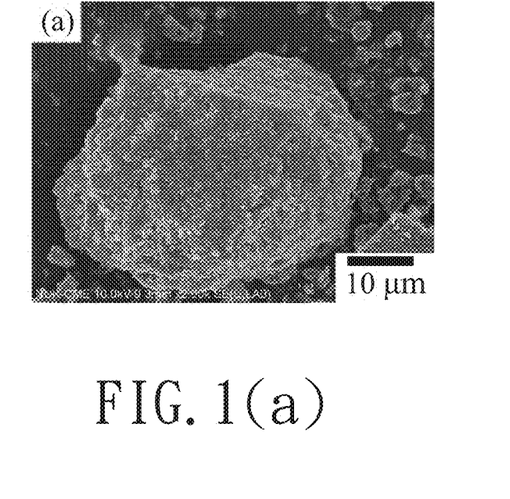
Figure 1B:
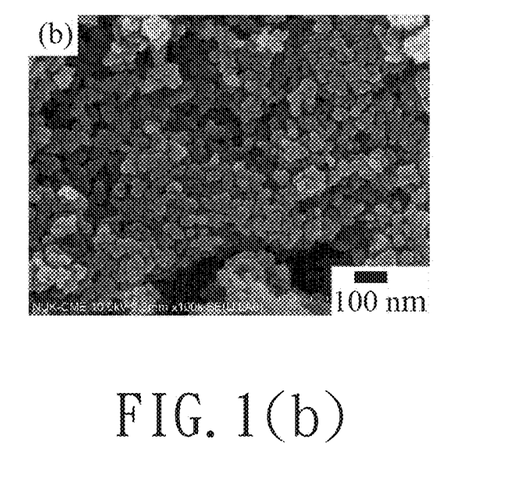

Please refer to FIG. 1, which shows scanning electron microscope photographs of the hydroxyapatite in the present invention. FIG. 1(a) is a 2,000× magnified photograph, and FIG. 1(b) is a 100,000× magnified photograph. According to FIG. 1, the crystal grains of the hydroxyapatite have sizes less than 100 nm which can be considered as nano-grade hydroxyapatite.

The precipitation method is used in the present invention for manufacturing hydroxyapatite which has advantages including:
1. The equipment used of the precipitation method is simple and low energy consumption which decreases production cost thereof.
2. The precipitation method has higher yield of hydroxyapatite.
3. By controlling parameters used in the precipitation method, the grain sizes of the hydroxyapatite obtained are smaller and a nano-grade hydroxyapatite is obtained. After the nano-grade hydroxyapatite is shaped and sintered, mechanical properties thereof are improved which is benefit for production a porous material. Furthermore, the diammonium hydrogen phosphate used in the present invention can stabilize the hydroxyapatite in an alkaline environment. Therefore, the diammonium hydrogen phosphate provides the alkaline environment and can be used for substitution phosphoric acid used in the conventional method for hydroxyapatite production.

Figure 2:
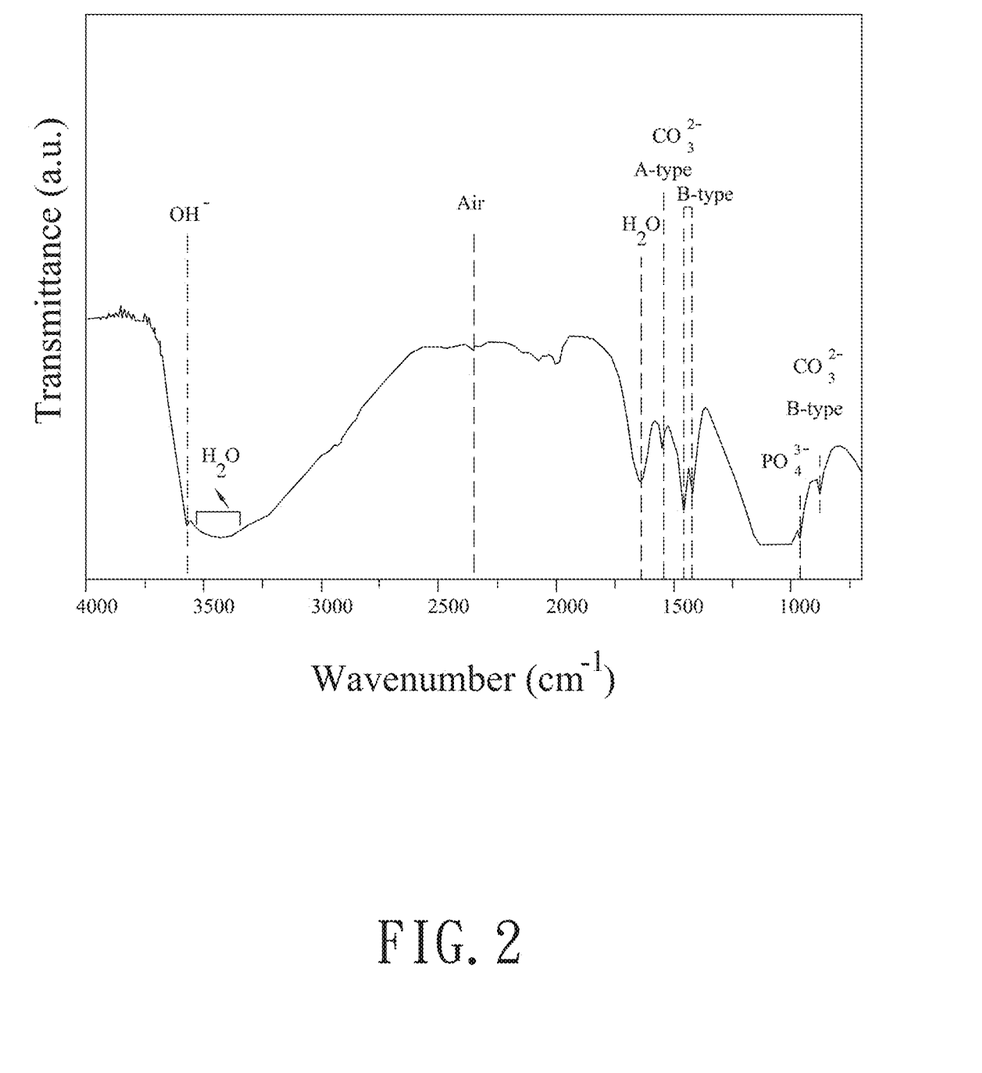
FIG. 2 is a Fourier-transform infrared spectroscopy analysis graph showing a hydroxyapatite powder in the present invention.

The hydroxyapatite obtained by the abovementioned method is analyzed by Fourier-transform infrared spectroscopy (FTIR). In FIG. 2, "A" represents "A-type carbonate" and "B" represents "B-type carbonate". A-type carbonate and B-type carbonate respectively represent substitution for hydroxide and substitution for phosphate. According to FIG. 2, carbonate ($CO_3^{2-}$) is detected by the FTIR which means that the hydroxyapatite of the present invention comprises carbonate ($CO_3^{2-}$). Therefore, the hydroxyapatite comprising carbonate of the present invention is similar to composition of human bones and has better biological performance.

Embodiment 2

Manufacturing of a Porous Bone Void Filler Material

Figure 3:
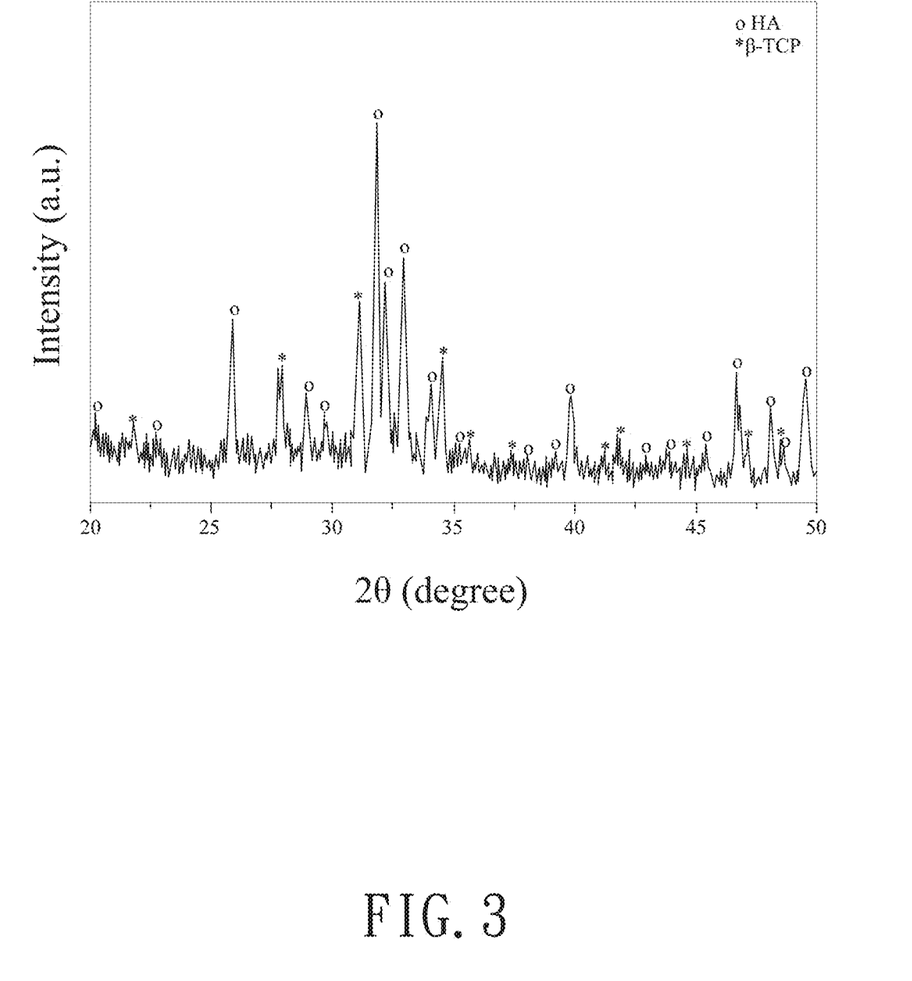
FIG. 3 is a X-Ray diffraction analysis graph showing a biphasic porous HA/β-TCP material in the present invention.

In the present embodiment, a pore former is utilized to manufacture a porous bone void filler material. The nano-grade hydroxyapatite in the Embodiment 1 is mixed with a pore former and a binder to obtain a porous calcium phosphate material such as the porous bone void filler in the present invention. In this embodiment, 35 wt % of stearic acid (pore former), 45 wt % of the hydroxyapatite and a remaining weight percentage of PVA (binder) are uniformly mixed to form a mixture. The mixture is placed into a mold for compression molding to obtain a compression-molded mixture, and then the compression-molded mixture is sintered at a sintering temperature. The sintering temperature is raised to 300-500° C. at a heating rate of 1-5° C./min and is maintained for 1-5 hours; and then the sintering temperature is raised to 1100-1300° C. at the heating rate of 1-5° C./min and is maintained for 5-30 hours to obtain a biphasic porous HA/β-TCP material. Referring to FIG. 3, the biphasic porous HA/β-TCP material is analyzed by X-ray diffraction (XRD) and structures of hydroxyapatite and β-TCP are detected at the same time. This result indicated that the crystalline phase of the porous bone void filler of the present invention is a biphasic HA/β-TCP. The biphasic HA/β-TCP has better degradability when applied on biomedical field.

Figure 4:
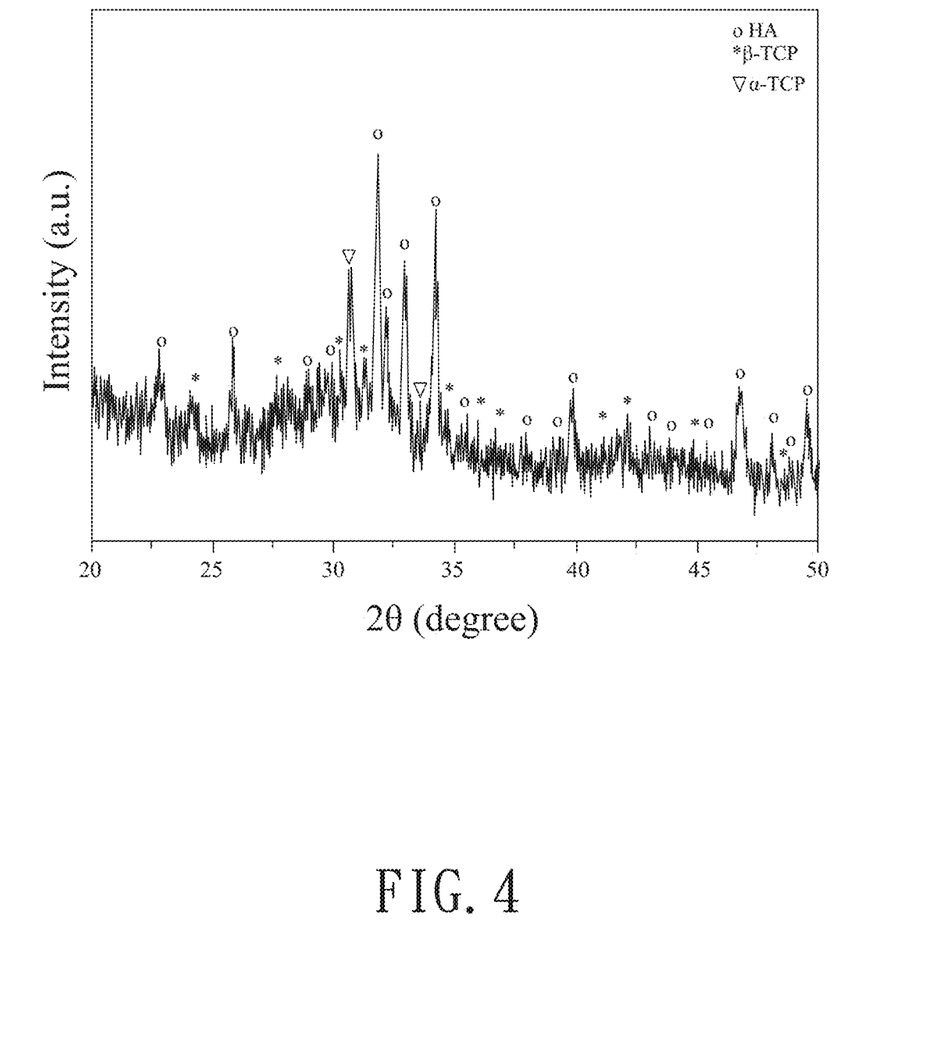
FIG. 4 is a X-Ray diffraction analysis graph showing a triphasic porous HA/β-TCP/α-TCP material in the present invention.

In a second embodiment, the sintering temperature is raised to 300-500° C. at a heating rate of 1-5° C./min and is maintained for 2-5 hours; and then the sintering temperature is raised to 1300-1500° C. at the heating rate of 1-5° C./min and is maintained for 1 to 10 hours to obtain a triphasic porous HA/β-TCP/α-TCP material. Referring to FIG. 4, the HA/β-TCP/α-TCP material is analyzed by X-ray diffraction (XRD) and structures of hydroxyapatite, β-TCP and α-TCP are detected at the same time. This result indicated that the crystalline phase of the porous bone void filler of the present invention is a triphasic HA/β-TCP/α-TCP. The triphasic HA/β-TCP/α-TCP has better degradability when applied on biomedical field. The triphasic HA/β-TCP/α-TCP can be used in dental fillings, orthopedic fillers and tissue engineering.

Moreover, the mold used in the present invention is designed according to requirements, and the compression-molded mixture of the present invention can be crushed and sieved after sintering to obtain the porous bone void fillers having different sizes. For example, the porous bone void filler can be porous particles having a diameter ranging from 0.5 mm to 2.0 mm or a porous scaffold have a diameter of 5 mm, a height of 7.5 mm and a porosity more than 38%.

Figure 5A:
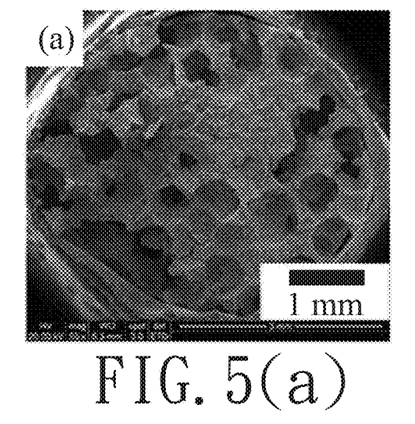
Figure 5B:
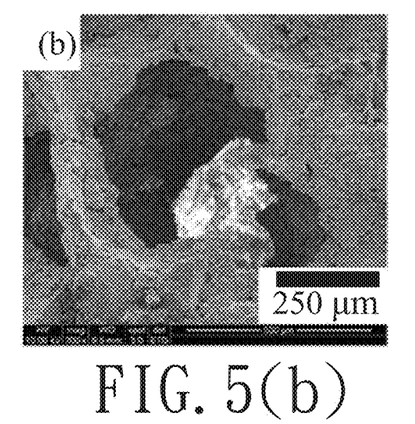
Figure 5C:
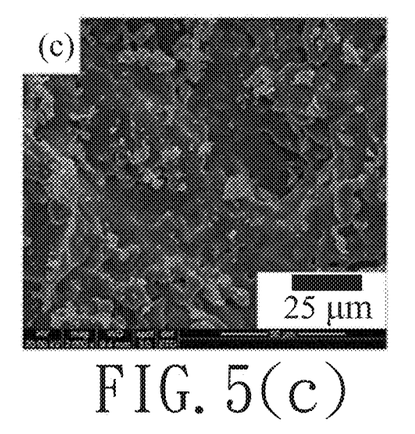

FIG. 5 shows scanning electron microscope photographs of a biphasic porous HA/β-TCP material in the present invention, in which FIG. 5(a) is a 55× magnified photograph, FIG. 5(b) is a 300× magnified photograph, and FIG. 5(c) is a 2000× magnified photograph. According to FIG. 5, a porous morphology of the porous bone void fillers of the present invention are observed. In FIG. 5(b), other pores can be observed from an internal of a pore. It indicated that pores in the biphasic porous HA/β-TCP material are communicated and enable to improve circulation of the body fluid and cell growth. FIG. 5(c) is a high magnified photograph for observation the morphology of the biphasic porous HA/β-TCP in detail.

Figure 6:
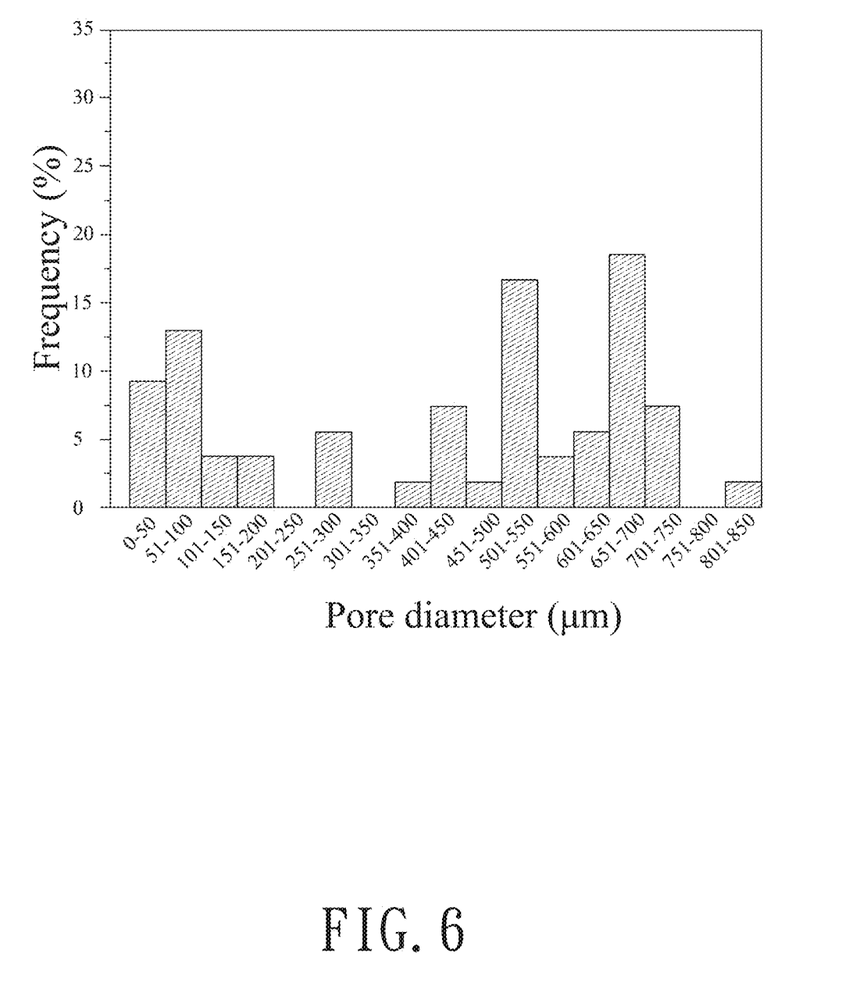
FIG. 6 is bar graph showing a pore size distribution of a biphasic porous HA/β-TCP material in the present invention.

FIG. 6 is bar graph showing a pore diameter distribution of the biphasic porous HA/β-TCP material in the present invention. FIG. 6 indicated that the HA/β-TCP material has large pores having diameter more than 100 μm and small pores having diameter less than 100 μm. The large pores provide spaces for cell growth and the small pores enable to improve fluid circulation.

Embodiment 3

Cell Viability Test

Figure 7:
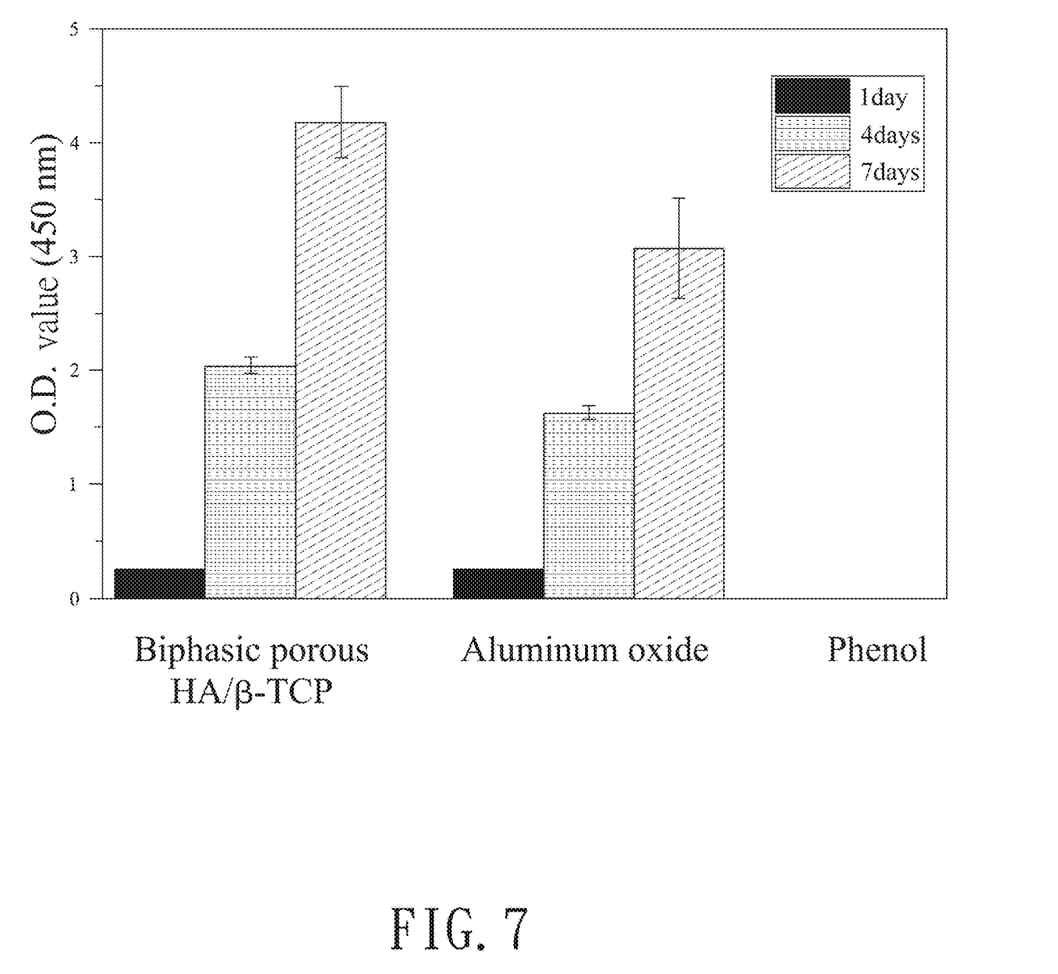
FIG. 7 is a bar graph showing cell viability of cells co-incubated with a biphasic porous HA/β-TCP material in the present invention.

Cell viability test in this embodiment is performed according to the protocol in ISO10993-5. MG-63 cells are co-incubated with the biphasic porous HA/β-TCP, phenol extract (positive control) and aluminum oxide (negative control) for 1 day, 4 days and 7 days. The cell viability is then tested by WST-1 cell viability assay. Referring to FIG. 7 and Table 1, cells incubated with the biphasic porous HA/β-TCP steadily grow as the cultivation time is increased which indicated that the biphasic porous HA/β-TCP of the present invention is not toxic to the cells. In addition, the cells incubated with the biphasic porous HA/β-TCP have higher O.D. 450 at different cultivation time compared to the cells co-incubated with aluminum oxide. This suggested that the biphasic porous HA/β-TCP may improve cell growth.

TABLE 1

| Cultivation time (day) | biphasic porous HA/β-TCP | aluminum oxide | phenol |
|---|---|---|---|
| Average value of O.D. (450 nm) | | | |
| 1 | 0.250333 | 0.2036 | 0.005167 |
| 4 | 2.0461 | 1.628367 | 0.0043 |
| 7 | 4.18 | 3.07 | 0.00 |
| Standard deviation | | | |
| 1 | 0.011143 | 0.014596 | 0.005526 |
| 4 | 0.073358 | 0.058692 | 0.000327 |
| 7 | 0.315318 | 0.438073 | 0.004446 |

Embodiment 4

Effect of Porous Bone Void Filler on Cell Survival and Cell Morphology

Figure 8:
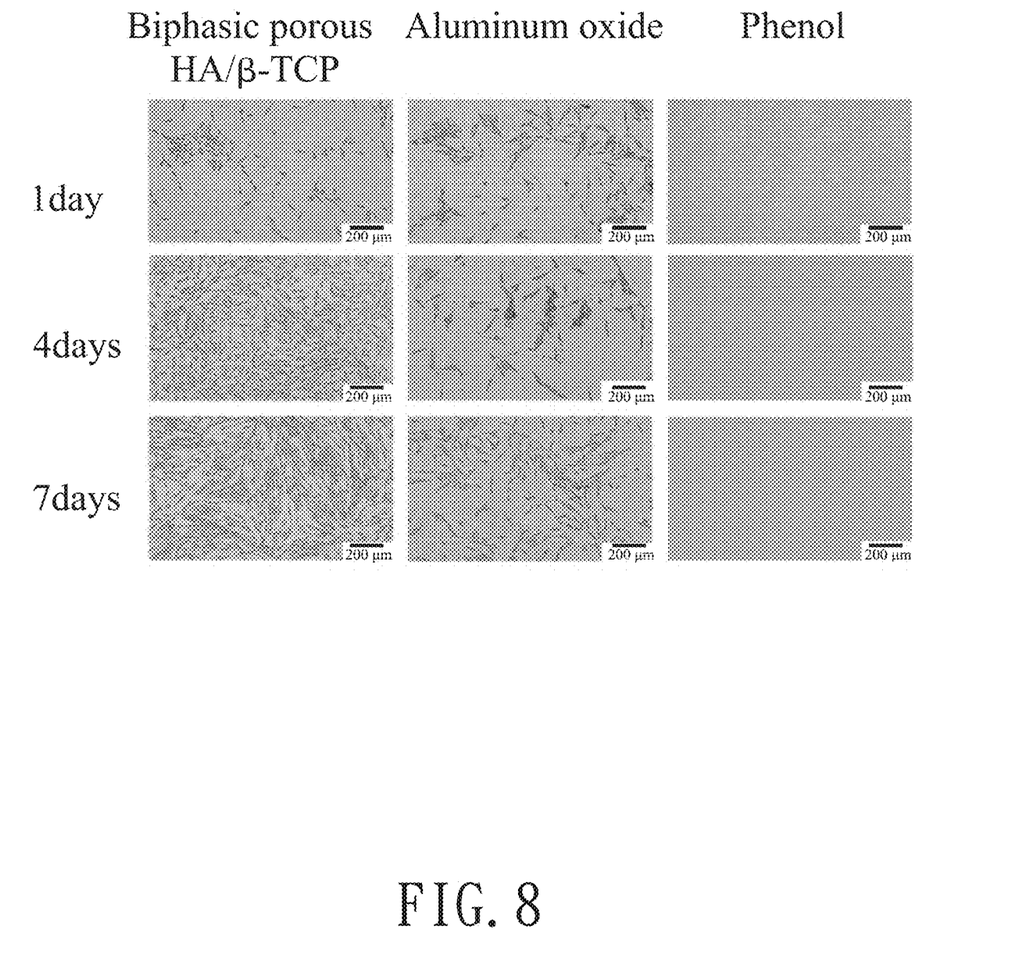
FIG. 8 shows optical microscope photographs of cell viability co-incubated with a biphasic porous HA/β-TCP material in the present invention.

MG-63 cells are co-incubated with the biphasic porous HA/β-TCP, phenol extract (positive control) and aluminum oxide (negative control) for 1 day, 4 days and 7 days. The cells were then observed by an optical microscope for observation cell survival and cell morphology. Referring to FIG. 8, the cells co-incubated with the biphasic porous HA/β-TCP are extended after 1 day-cultivation which indicated that the cells are attached excellently. After cultivation for 4 days, the number of the cells co-incubated with the biphasic porous HA/β-TCP is significantly increased and is much higher than the cell number of the cells co-incubated with aluminum oxide. After cultivation for 7 days, the number of the cells co-incubated with the biphasic porous HA/β-TCP is continuously increased and is still higher than the cell number of the cells co-incubated with aluminum oxide. In addition, some of the cells co-incubated with the biphasic porous HA/β-TCP are stacked on other cells, but all the cells still have a spinning morphology. It indicated that the cells are still healthy after co-incubated with the biphasic porous HA/β-TCP for 7 days. All of the cells co-incubated with the phenol extract are not survival. The result indicated that the biphasic porous HA/β-TCP of the present invention has great biocompatibility.

Embodiment 5

Animal Experiment

Figure 9:
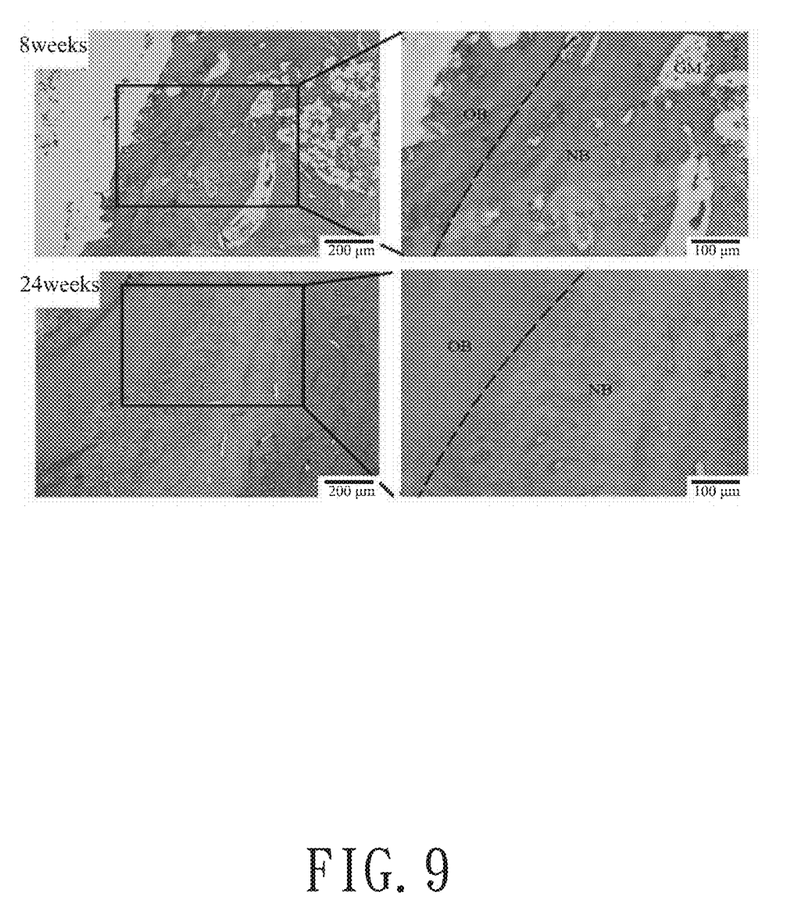
FIG. 9 shows hematoxylin and eosin staining photographs of a New Zealand White rabbit's thigh bone implanted with a biphasic porous HA/β-TCP material in the present invention.

The biphasic porous HA/β-TCP material is implanted into a thigh bone of New Zealand White rabbit. After 8 weeks and 24 weeks of implantation, the thigh bone of the rabbit is collected and sliced for staining with hematoxylin and eosin (H&E stain), and then the biopsies are observed by the optical microscope at 100× magnification and 200× magnification. Referring to FIG. 9, after 8 weeks of implantation, there are no significant gaps at an interface (marked by the dash line) between the thigh bone of the host and a defect area which indicated that the biphasic porous HA/β-TCP material makes the new bone (NB) growth excellently. In addition, the "OB" in the photograph represents "osteoblast", and the "GM" represents "grafted material". Furthermore, the biphasic porous HA/β-TCP material is significantly degraded and a lot of new bones are formed inside the bone, this indicated that the defect area is filled up by the new bone so as to replace a space filled with the biphasic porous HA/β-TCP material. After 24 weeks of incubation, the new bone is extended to an internal of the defect area and bon tissue of the new bone becomes more compact. The defect area is healed excellently and the new bone is gradually mineralized and became a mature lamellar bone. In addition, it is hard to distinguish the interface (marked by the dash line) between the thigh bone of the host and the defect area. Therefore, the biphasic porous HA/β-TCP material has great effect on inducing osteogenesis and improving bone tissue formation.

According to the abovementioned embodiments, the present invention has the advantages below compared to the prior art:

1. In the present invention, the natural calcium-containing waste are mixed with the phosphorus-containing and then processed by the precipitation method to synthesize nano-grade hydroxyapatite. Compared to the commonly used hydrothermal method, the present invention has advantages of high yield, low energy consumption, simple equipment and low production cost. In addition, the hydroxyapatite manufactured by the present invention comprises carbonate which is closer to the composition of human bones.
2. The waste egg shells are utilized to manufacture bone void fillers including porous particles and porous scaffolds in the present invention which achieved purpose of recycling waste and reducing production cost.
3. The present invention utilized pore former to manufacture the bone void filler and the mold used in the present invention can be designed according to requirements. Therefore, different sized of the porous bone void fillers are obtained by the present invention. In addition, the pores of the bone void fillers are communicated by using the pore former, and the diameter of the pores can be controlled by the pore former.

What is claimed is:

1. A method for manufacturing a bone void filler by a natural calcium-containing waste, comprising steps of:
    (a) uniformly mixing 5-20 wt % of a powder of calcium-containing waste, 5-20 wt % of acetic acid and a remaining weight percentage of water to obtain a mixing solution, wherein the powder of calcium-containing waste comprises an eggshell powder, a shell powder of *Crustacea* animals, a shell powder of *Bivalvia* animals or a shell powder of *Gastropoda* animals;
    (b) adding 5-20 vol % of a diammonium hydrogen phosphate solution into the mixing solution to obtain a suspension;
    (c) controlling a pH value of the suspension between 7.5 and 14 to obtain an alkaline solution;
    (d) leaving the alkaline solution at room temperature for precipitation for 0.1-72 hours, preforming a centrifugal process or a suction filtration process on the alkaline solution to obtain a precipitate, drying and grinding the precipitate to obtain a hydroxyapatite; and (e) uniformly mixing 30-60 wt % of a pore former, 30-60 wt % of the hydroxyapatite and a remaining weight percentage of a binder to form a mixture, compression molding the mixture in a mold and then sintering the compression-molded mixture at a sintering temperature to obtain the bone void filler.

2. The method as claimed in claim 1, wherein in the step (e), the sintering temperature is raised to 200-500° C. at a heating rate of 1-5° C./min and is maintained for 1-5 hours; and then the sintering temperature is raised to 1000-1300° C. at the heating rate of 1-5° C./min and is maintained for 5-30 hours to obtain a biphasic material.

3. The method as claimed in claim 2, wherein the pore former is selected from a group consisting of polyvinylpyrrolidone, poly (lactic-co-glycolic acid), stearic acid, sucrose and graphite, and wherein the binder is selected from a group consisting of starch, paraffin, carboxymethyl cellulose and poly(vinyl alcohol).

4. A bone void filler manufactured by the method as claimed in claim 3.

5. A bone void filler manufactured by the method as claimed in claim 2.

6. The method as claimed in claim 1, wherein in the step (e), the sintering temperature is raised to 300-500° C. at a heating rate of 1-5° C./min and is maintained for 2-5 hours; and then the sintering temperature is raised to 1300-1500° C. at the heating rate of 1-5° C./min and is maintained for 1-10 hours to obtain a triphasic material.

7. A bone void filler manufactured by the method as claimed in claim 6.

8. The method as claimed in claim 1, wherein the *Crustacea* animals comprises crabs, shrimps, lobsters, crayfishes and hills, wherein the *Bivalvia* animals comprises *Ostreoida* animals and *Venerida* animals, and wherein the *Gastropoda* animals comprises *Haliotidae* animals.

9. A bone void filler manufactured by the method as claimed in claim 8.

10. A bone void filler manufactured by the method as claimed in claim 1.

* * * * *